United States Patent
Schellin et al.

(10) Patent No.: US 9,877,722 B2
(45) Date of Patent: Jan. 30, 2018

(54) DEVICES AND METHODS FOR GUIDING SURGICAL FASTENERS

(71) Applicant: Ethicon LLC, Guaynabo, PR (US)

(72) Inventors: Emily A. Schellin, Cincinnati, OH (US); Jeffrey S. Swayze, West Chester, OH (US); Jerome R. Morgan, Cincinnati, OH (US); Frederick E. Shelton, IV, Hillsboro, OH (US); Gary W. Knight, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 551 days.

(21) Appl. No.: 14/474,805

(22) Filed: Sep. 2, 2014

(65) Prior Publication Data
US 2016/0058448 A1    Mar. 3, 2016

(51) Int. Cl.
*A61B 17/068* (2006.01)
*A61B 17/064* (2006.01)
*A61B 17/10* (2006.01)
*A61B 17/072* (2006.01)
(Continued)

(52) U.S. Cl.
CPC .......... *A61B 17/105* (2013.01); *A61B 17/064* (2013.01); *A61B 17/068* (2013.01); *A61B 17/0644* (2013.01); *A61B 17/07207* (2013.01); *A61B 17/07292* (2013.01); *A61B 2017/07271* (2013.01); *A61B 2017/07278* (2013.01); *A61B 2017/2933* (2013.01); *A61B 2017/2936* (2013.01); *A61B 2090/037* (2016.02)

(58) Field of Classification Search
CPC ... A61B 17/105; A61B 17/064; A61B 17/068; A61B 2017/07271; A61B 2090/037; A61B 2017/07278; A61B 2017/2933; A61B 2017/2936

USPC .......................................... 227/176.1, 177.1
See application file for complete search history.

(56) References Cited

U.S. PATENT DOCUMENTS 5,465,895 A    11/1995    Knodel et al.
5,503,638 A     4/1996    Cooper et al.
5,725,536 A     3/1998    Oberlin et al.
(Continued)

FOREIGN PATENT DOCUMENTS

WO    WO-2009033057 A2    3/2009
WO    WO-2013151820 A1    10/2013

OTHER PUBLICATIONS

"MicroCutter XCHANGE™ 30." Inservice Poster. (Oct. 13).
(Continued)

*Primary Examiner* — Michelle Lopez
(74) *Attorney, Agent, or Firm* — Mintz Levin Cohn Ferris Glovsky and Popeo, P.C.

(57) ABSTRACT

Devices and methods are provided for guiding surgical fasteners. In general, the devices and methods can facilitate guidance of fasteners during deployment of the fasteners into tissue. In general, the surgical device can include one or more guidance features configured to facilitate guidance of the fasteners during ejection of the fasteners from the cartridge. The one or more guidance features can be configured to reduce lateral movement of the fasteners during deployment thereof. In an exemplary embodiment, each of the one or more guidance features can be configured to support a fastener on three sides thereof during deployment of the fastener. The one or more guidance features can be formed on the cartridge, e.g., formed on a surface thereof or formed on a sled disposed in the cartridge, and/or can be formed on a jaw that seats the cartridge.

5 Claims, 9 Drawing Sheets

(51) Int. Cl.
*A61B 17/29* (2006.01)
*A61B 90/00* (2016.01)

(56) References Cited

U.S. PATENT DOCUMENTS

| | | | |
|---|---|---|---|
| 7,000,818 B2 | 2/2006 | Shelton, IV et al. |
| 7,473,258 B2 | 1/2009 | Clauson et al. |
| 7,533,790 B1 | 5/2009 | Knodel et al. |
| 7,641,671 B2 | 1/2010 | Crainich |
| 7,669,746 B2 | 3/2010 | Shelton, IV |
| 7,678,121 B1 | 3/2010 | Knodel |
| 7,753,250 B2 | 7/2010 | Clauson et al. |
| 7,918,376 B1 | 4/2011 | Knodel et al. |
| 7,954,683 B1 | 6/2011 | Knodel et al. |
| 7,963,432 B2 | 6/2011 | Knodel et al. |
| 7,988,026 B2 | 8/2011 | Knodel et al. |
| 8,056,789 B1 | 11/2011 | White et al. |
| 8,066,720 B2 | 11/2011 | Knodel et al. |
| 8,070,034 B1 | 12/2011 | Knodel |
| 8,070,036 B1 | 12/2011 | Knodel |
| 8,087,562 B1 | 1/2012 | Manoux et al. |
| 8,123,795 B1 | 2/2012 | Knodel et al. |
| 8,225,980 B1 | 7/2012 | Rivera |
| 8,261,958 B1 | 9/2012 | Knodel |
| 8,272,551 B2 | 9/2012 | Knodel et al. |
| 8,317,071 B1 | 11/2012 | Knodel |
| 8,317,072 B1 | 11/2012 | Knodel et al. |
| 8,356,740 B1 | 1/2013 | Knodel |
| 8,357,174 B2 | 1/2013 | Roth et al. |
| 8,365,973 B1 | 2/2013 | White et al. |
| 8,403,956 B1 | 3/2013 | Thompson et al. |
| 8,439,245 B2 | 5/2013 | Knodel et al. |
| 8,439,246 B1 | 5/2013 | Knodel |
| 8,496,155 B2 | 7/2013 | Knodel |
| 8,505,800 B1 | 8/2013 | Knodel et al. |
| 8,556,153 B1 | 10/2013 | Knodel |
| 8,631,992 B1 | 1/2014 | Hausen et al. |
| 8,636,189 B1 | 1/2014 | Knodel et al. |
| 8,679,155 B2 | 3/2014 | Knodel et al. |
| 8,701,960 B1 | 4/2014 | Manoux et al. |
| 2009/0065552 A1 | 3/2009 | Knodel et al. |
| 2010/0155453 A1 | 6/2010 | Bombard et al. |
| 2011/0204120 A1 | 8/2011 | Crainich |
| 2012/0010652 A1 | 1/2012 | Hahnen et al. |
| 2012/0241497 A1 | 9/2012 | Mandakolathur Vasudevan et al. |
| 2013/0277410 A1 | 10/2013 | Fernandez et al. |
| 2014/0041191 A1 | 2/2014 | Knodel |
| 2014/0175146 A1 | 6/2014 | Knodel |

OTHER PUBLICATIONS

"MicroCutter XCHANGE™ 30." Instructions for Use. (2014).
"MicroCutter XCHANGE® 30 Videos." Cardica. Web. May 7, 2014. http://www.cardica.com/inservice-guide.php.
"MicroCutter XCHANGE® 30: The World's First and Only Articulating 5mm Stapler." Cardica. Web. May 7, 2014. http://www.cardica.com/minimally-invasive-surgery.php.
U.S. Appl. No. 14/300,954, filed Jun. 10, 2014.
European Search Report for Application No. 15183384.5 dated May 17, 2016.

DEVICES AND METHODS FOR GUIDING SURGICAL FASTENERS

FIELD OF THE INVENTION

The present disclosure relates generally to guiding surgical fasteners.

BACKGROUND

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

A surgical fastening device includes an elongate shaft and an end effector coupled to a distal end of the elongate shaft. The end effector includes first and second opposed jaws coupled to one another and configured to engage tissue therebetween. The device also includes a staple cartridge disposed within the first jaw. The staple cartridge also includes a plurality of staple-receiving recesses formed therein, a plurality of D-shaped staples configured to rotate about a pivot point into tissue engaged between the first and second jaws, wherein each staple is disposed within a staple-receiving recess, and a plurality of guide members formed on the cartridge. Each guide member extends from a surface of the cartridge at a location adjacent to a staple-receiving recess, and each guide member has an inner arcuate surface configured to guide a leg of a staple along an arcuate path and into tissue engaged between the first and second jaws. In a further aspect, each guide member includes opposed sidewalls configured to support and maintain alignment of a staple being rotatably advanced therethrough.

Each guide member is formed on and protrudes outward from a tissue-contacting surface of the cartridge. Further, each guide member can be formed on an inwardly-facing surface of the cartridge, opposite to a tissue-contacting surface. In one aspect each guide-member is substantially U-shaped such that the guide member is configured to contact three sides of a staple being advanced therethrough.

According to another aspect, a surgical stapling device comprises an elongate shaft having an end effector coupled to a distal end thereof and including a cartridge-receiving jaw and an anvil pivotally coupled to the cartridge-receiving jaw. The device also includes a staple cartridge disposed within the cartridge-receiving jaw, wherein the staple cartridge has a carrier disposed therein with a plurality of plastically deformable staples formed on the carrier. The staple cartridge also has a deck with a plurality of openings formed therein, wherein each opening is configured to receive one of the plurality of staples therethrough. Each opening further has a guide member extending outwardly from the deck that is configured to guide a staple being advanced through the opening along an arcuate path.

Each guide member can extend outwardly from the deck in a direction toward the anvil. Alternatively, each guide member can extend outwardly from the deck in a direction away from the anvil.

In one aspect, each guide member includes opposed sidewalls that engage opposed sides of a staple being advanced therethrough. Further, each guide member can include a curved inner surface that guides the staples along a curved pathway.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
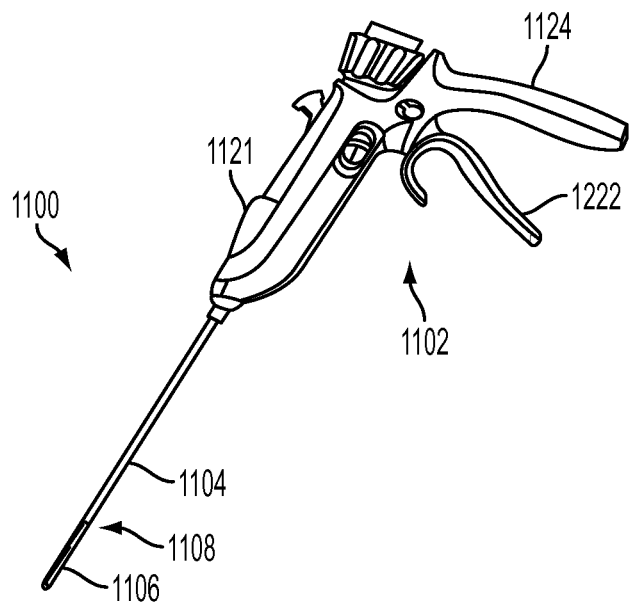
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
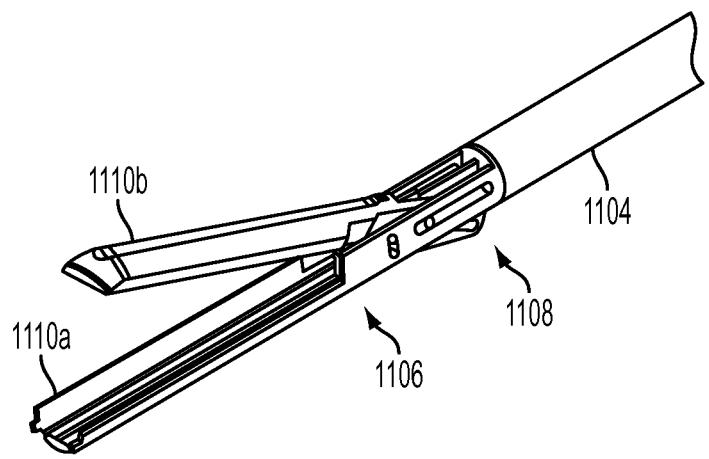
FIG. 2 is a perspective view of the end effector of FIG. 1 in an open position.
Figure 3:
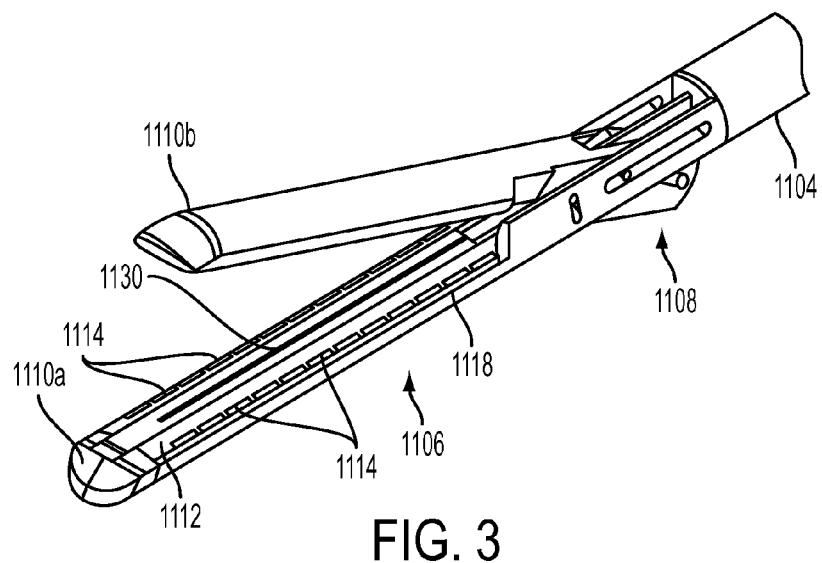
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
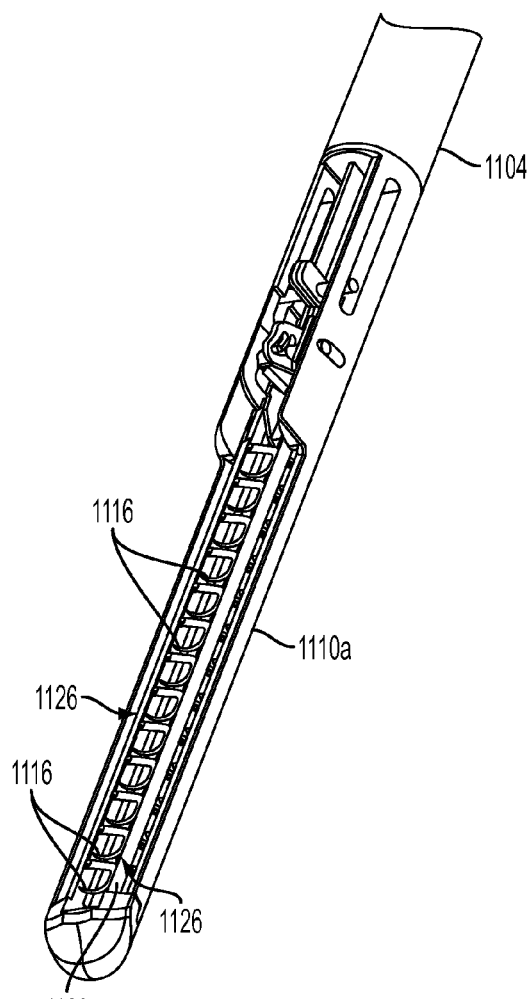
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
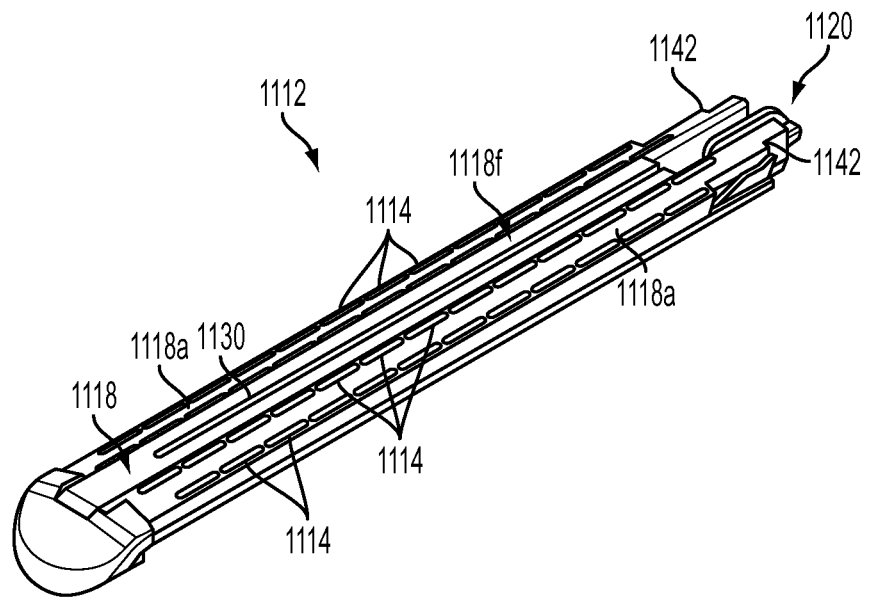
FIG. 5 is a perspective view of the cartridge of FIG. 3.
Figure 6:
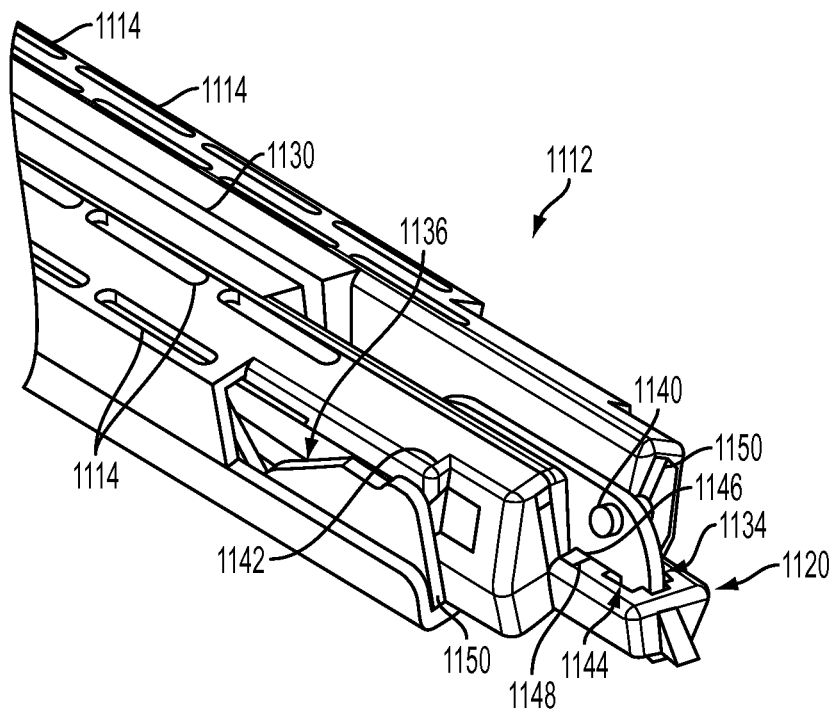
FIG. 6 is another perspective view of the cartridge of FIG. 3.
Figure 7:
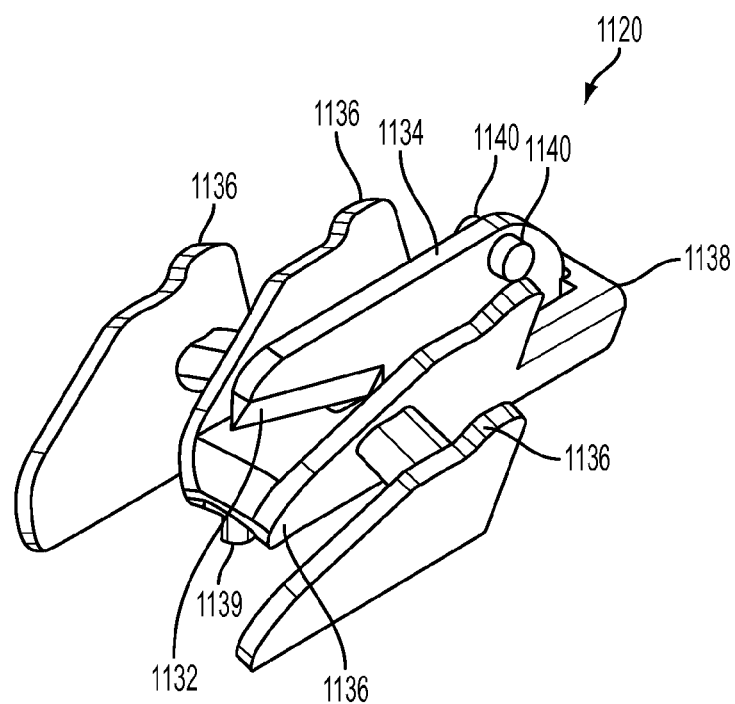
FIG. 7 is a perspective view of a sled of the cartridge of FIG. 3, the sled including a cutting element, and the cutting element being in a first position.
Figure 8:
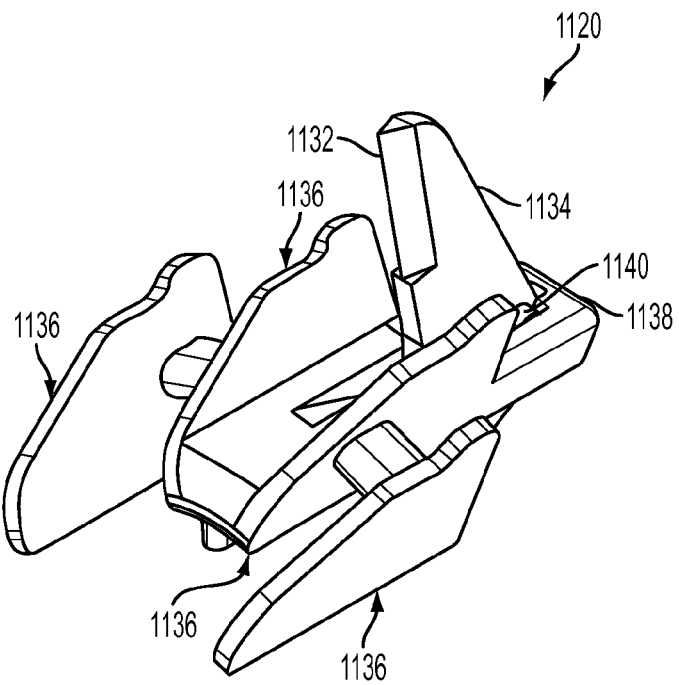
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110*b* through the openings 1114 and deform against the second jaw 1110*b*. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to facilitate guidance of fasteners during deployment of the fasteners into tissue. In general, the surgical device can include one or more guidance features configured to facilitate guidance of the fasteners during ejection of the fasteners from the cartridge. The one or more guidance features can be configured to reduce lateral movement of the fasteners during deployment thereof, thereby allowing the fasteners to be more accurately positioned within the tissue relative to one another and relative to the tissue. By helping to guide the fastener into the tissue, the fastener can be less likely to skew laterally during deployment into the tissue due to resistance of the tissue and/or tissue flow can be reduced during fastener deployment. The fasteners can thus be effectively positioned relative to one another and to the tissue to facilitate proper healing and/or sealing of the tissue. This can be particularly beneficial in relatively thick tissue because the tissue can provide relatively high resistance to the fastener being deployed therein. In an exemplary embodiment, each of the one or more guidance features can be configured to support a fastener on three sides thereof during deployment of the fastener, thereby helping to minimize lateral movement of the fastener during the deployment. The one or more guidance features can be formed on the cartridge, e.g., formed on a surface thereof or formed on a sled disposed in the cartridge, and/or can be formed on a jaw that seats the cartridge.

A surgical device can be configured to guide fasteners during deployment thereof in a variety of ways. In the embodiments described below, staples are used as examples of fasteners, but as will be appreciated by a person skilled in the art, other types of fasteners can be similarly configured and used.

Figure 9:
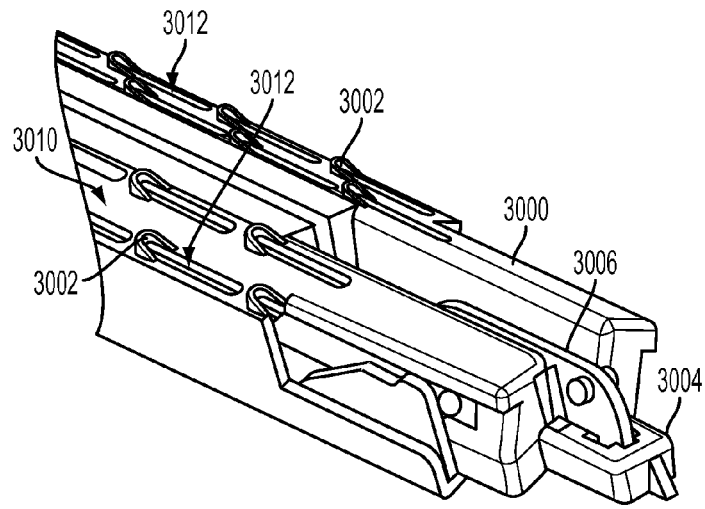
FIG. 9 is a perspective view of one embodiment of a cartridge including a plurality of guidance features and having a plurality of fasteners disposed therein.
Figure 10:
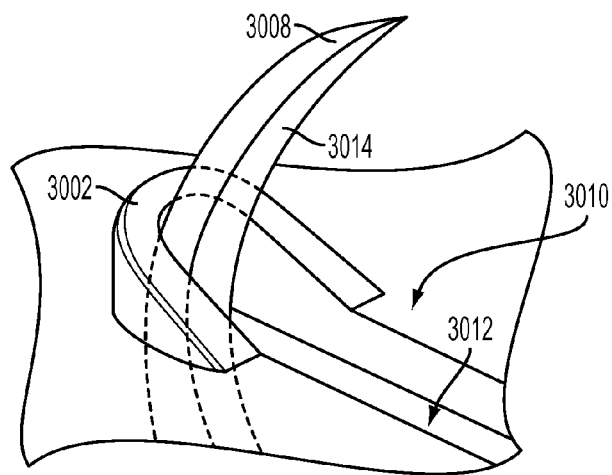
FIG. 10 is a perspective view of one of the fasteners of FIG. 9 being deployed and guided by one of the guidance features.

In some embodiments, a cartridge having a plurality of fasteners disposed therein can include one or more guidance features, also referred to herein as "guide members," configured to guide the fasteners during firing of the fasteners from the cartridge. As discussed herein, the cartridge can be configured to be removably and replaceably seated in an end effector of a surgical device. FIG. 9 and FIG. 10 illustrate one embodiment of a cartridge 3000 that includes a plurality of fasteners 3008 disposed therein, a sled 3004 including a movable cutting element 3006, and one or more guide members 3002 configured to guide the fasteners 3008 during firing of the fasteners 3008 from the cartridge 3000. In this illustrated embodiment, the fasteners 3008 include staples similar to the above-mentioned staples 1116, but as also mentioned above, other types of staples or fasteners can be used. As in this illustrated embodiment, the one or more guide members 3002 can each be formed on and protrude upward from a tissue-engaging surface 3010 of the cartridge 3000, e.g., in a direction toward an anvil (not shown) of the surgical device. The guidance provided by the guide members 3002 can thus be provided after the fasteners 3008 have at least partially exited their respective fastener-receiving recesses 3012 so as to pass above the tissue-engaging surface 3010. The guide members 3002 protrude upward from the tissue-engaging surface 3010 can allow the guide members 3002 to be located in a gap of space between the tissue-engaging surface 3010 and a tissue-engaging surface (not shown) of the anvil, which can help grip tissue positioned within the gap of space. Movement or flow of the tissue within the gap of space can thus be reduced, which can allow the tissue to be more effectively fastened.

The guide members 3002 can have a variety of sizes, shapes, and configurations. Each of the guide members 3002 can have an inner arcuate surface, as in this illustrated embodiment. The inner arcuate surface can be configured to guide a second leg 3014 of the staple 3008 along an arcuate path as the staple 3008 is being deployed into a tissue (not shown). As discussed herein, the staple 3008 can also include a substantially straight first leg (not shown) connected to the curved second leg 3014. The inner arcuate surface of each of the guide members 3002 can be shaped to mimic a curvature of the fastener's second leg 3014, thereby helping to maximize an amount of movement support for the fastener 3008 during deployment thereof. As in this illustrated embodiment, the guide members 3002 can each be U-shaped with opposed sidewalls and a curved intermediate portion connecting the sidewalls. As shown in FIG. 10, the sidewalls can be configured to support and maintain alignment of the fastener during deployment. Being opposed, the sidewalls can help prevent lateral movement of the fastener 3008 during deployment. As shown in FIG. 10, the opposed sidewalls and the curved intermediate portion can be configured to contact three sides of the fastener 3008 as the fastener is guided by the guide member 3002 during deployment, thereby helping to prevent lateral movement of the fastener 3008 due to the sidewalls and helping to prevent distal movement of the fastener 3008 due to the intermediate portion.

Each of the guide members 3002 can be formed adjacent to and on a distal side of their respective fastener-receiving recesses 3012, as shown in this illustrated embodiment. In this way, when the fasteners 3008 are driven out of the cartridge 3000 in response to distal translation of the sled 3004 through the cartridge, the guide members 3002 can be configured to guide their respective fasteners' second legs 3014 as the second legs 3014 rotate out of the cartridge 3002 to lead the fasteners 3008 out of the cartridge 3002.

In the embodiment of FIG. 9, the one or more guide members 3002 are located above the tissue-engaging surface 3010. In other embodiments, a cartridge can include one or more guide members located below a tissue-engaging surface of the cartridge. Being located below the tissue-engaging surface can help prevent the guide members from snagging on and/or otherwise interfering with tissue engaged by the cartridge and/or from affecting an amount of space between facing tissue engagement surfaces of an end effector within which tissue can be positioned and clamped. In some embodiments, a cartridge can include one or more guide members that are located both above and below a tissue-engaging surface thereof.

Figure 11:
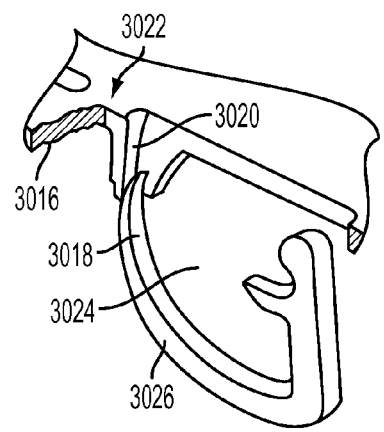
FIG. 11 is a perspective, partially cross-sectional view of another embodiment of a cartridge including a plurality of guidance features and having a plurality of fasteners disposed therein.
Figure 12:
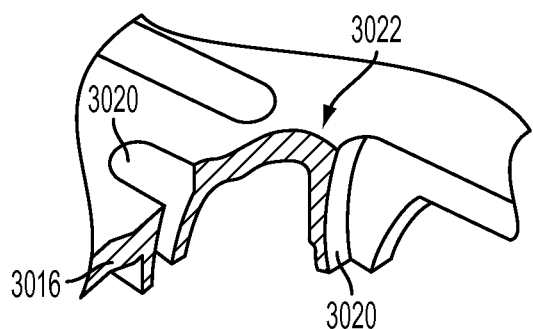
FIG. 12 is another perspective, partially cross-sectional view of the cartridge of FIG. 11 without the fasteners disposed therein.
Figure 13:
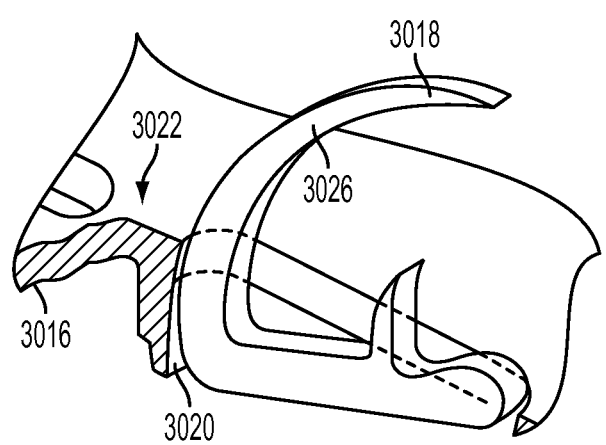
FIG. 13 is another perspective, partially cross-sectional view of the cartridge of FIG. 11 with one of the fasteners being deployed and guided by one of the guidance features.

FIG. 11, FIG. 12, and FIG. 13 illustrate another embodiment of a cartridge 3016 that includes a plurality of fasteners 3018 disposed therein, a sled (not shown), and one or more guide members 3020 configured to guide the fasteners 3018 during firing of the fasteners 3018 from the cartridge 3016. The fasteners 3018, the cartridge 3016, and the guide members 3020 can be generally configured and used similar to the fasteners 3008, the cartridge 3000, and the guide members 3002, respectively, of FIG. 9 and FIG. 10. In this illustrated embodiment, however, the one or more guide members 3020 are each located below a tissue-engaging surface 3022 of the cartridge 3016 and are each formed adjacent to and on a distal side of a staple-receiving recess 3024. Similar to the guide members 3002 of FIG. 9, the guide members 3020 can each include opposed sidewalls (best shown in FIG. 12) and an inner arcuate surface shaped to mimic a curvature of the fastener's second leg 3026, thereby allowing the guide members 3020 to support their associated fasteners 3008 on three sides thereof during fastener deployment.

As discussed above, one or more guide members can be formed on a surface of a cartridge. In other embodiments, as mentioned above, a cartridge can include one or more guide members formed on a sled disposed within the cartridge and configured to translate therethrough to drive fasteners out of the cartridge. The sled can thus be configured to support and maintain alignment of fasteners being deployed in response to the sled's translation relative thereto. The sled including guidance features can help allow existing cartridges to be only slightly modified, or not modified at all, in order to include guidance features because the sleds including guidance features can be incorporated into the existing cartridges.

Figure 14:
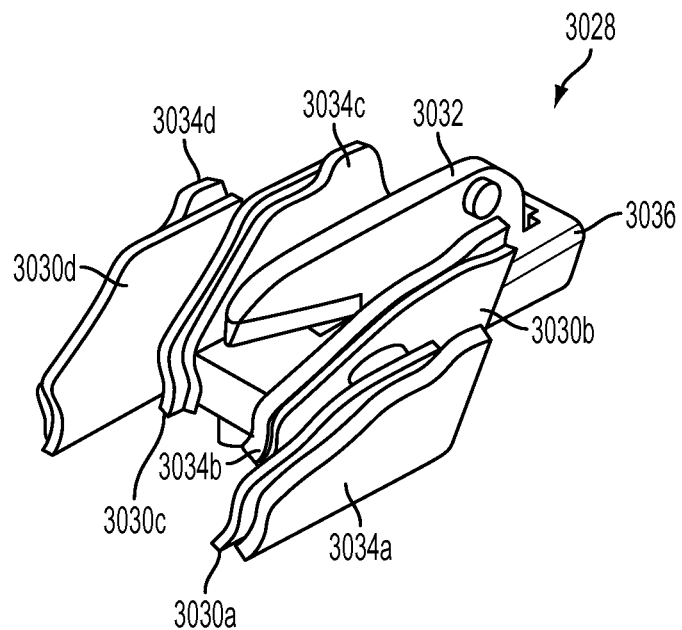
FIG. 14 is a perspective view of one embodiment of a sled that includes a plurality of guidance features.
Figure 15:
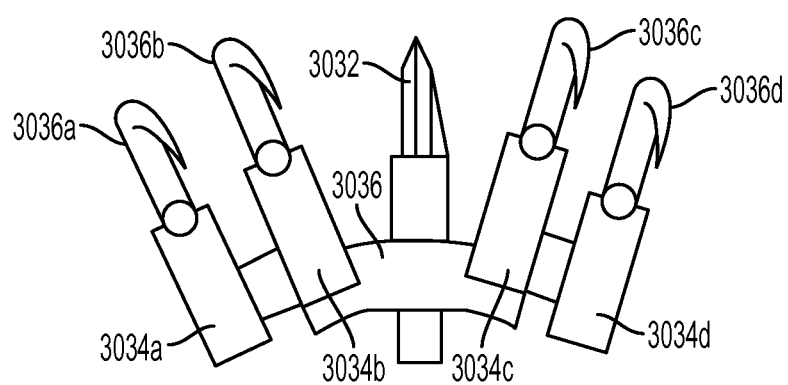
FIG. 15 is an end view of the sled of FIG. 14 with a plurality of fasteners engaged with the plurality of guidance features.
Figure 16:
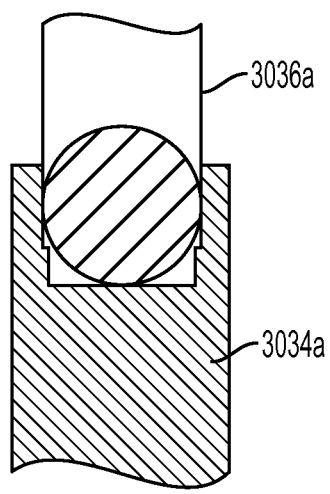
FIG. 16 is a cross-sectional view of one of the fasteners and one of the guidance features of FIG. 15.

FIG. 14 illustrates one embodiment of a sled 3028 that includes one or more guide members 3030a, 3030b, 3030c, 3030d, a cutting element 3032 configured to move between first and second positions, one or more wedges 3034a, 3034b, 3034c, 3034d configured to drive fasteners from the cartridge, and a base 3036. The sled 3028 can be used with any of the cartridges discussed herein. Each of the wedges 3034a, 3034b, 3034c, 3034d can have one of the guide members 3030a, 3030b, 3030c, 3030d associated therewith. Thus, a number of the wedges 3034a, 3034b, 3034c, 3034d can equal a number of the guide members 3030a, 3030b, 3030c, 3030d. As in this illustrated embodiment, as also shown in FIG. 15 and FIG. 16, the guide members 3030a, 3030b, 3030c, 3030d can include lateral guide walls of the wedges 3034a, 3034b, 3034c, 3034d. The guide walls can be configured to provide lateral support to fasteners being deployed by the sled 3028 via engagement with the wedges 3034*a*, 3034*b*, 3034*c*, 3034*d*. Without the guide walls, the fastener may only receive guidance from a pivot point about which the fastener rotates during deployment thereof. This pivot point, however, is weak when the fastener is configured to break off from the pivot point during fastening, such as with the fasteners 1116 in the above-mentioned device 1100.

As shown in FIG. 15 and FIG. 16, when the sled 3028 engages fasteners 3036*a*, 3036*b*, 3036*c*, 3036*d* so as to push and deploy the fasteners 3036*a*, 3036*b*, 3036*c*, 3036*d*, the guide walls defined by the guide members 3030*a*, 3030*b*, 3030*c*, 3030*d* can engage the fasteners 3036*a*, 3036*b*, 3036*c*, 3036*d* and provide directional movement guidance such that lateral movement of the fasteners 3036*a*, 3036*b*, 3036*c*, 3036*d* can be minimized. In this illustrated embodiment, the fasteners 3036*a*, 3036*b*, 3036*c*, 3036*d* include staples similar to the above-mentioned staples 1116, but as also mentioned above, other types of staples or fasteners can be used.

As discussed above, one or more guide members can be formed on a surface of a cartridge and/or can be formed on a sled. In other embodiments, as mentioned above, a jaw that seats a cartridge, e.g., a jaw configured to releasably and replaceably receive a cartridge, can include one or more guide members. The jaw, and hence an end effector that includes the jaw, can thus be configured to support and maintain alignment of fasteners being deployed therefrom. The jaw including guidance features can help allow existing cartridges to be used with a device including guidance features without the cartridges having to be modified.

Figure 17:
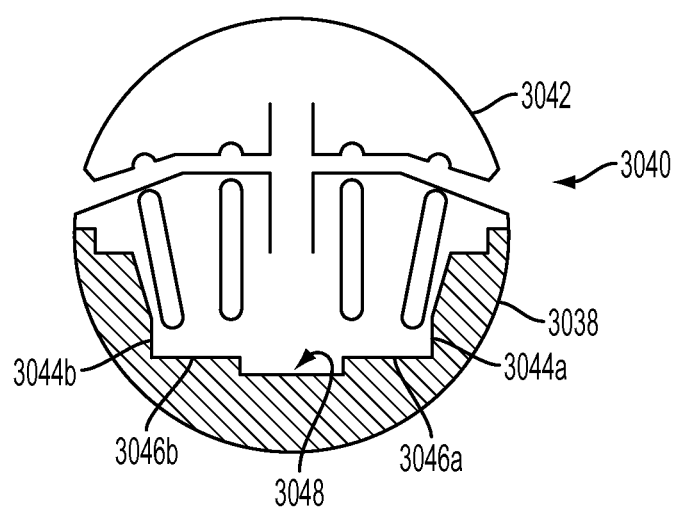
FIG. 17 is a cross-sectional view of one embodiment of a bottom jaw that includes a plurality of guidance features, the bottom jaw being part of an end effector that also includes an upper jaw.
Figure 18:
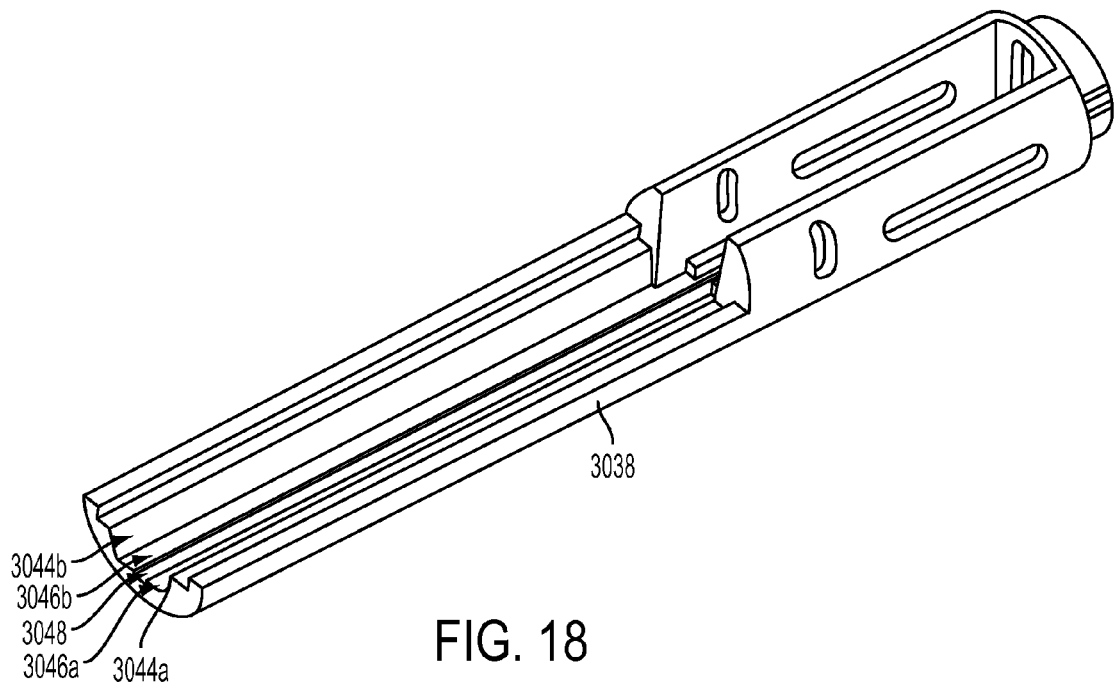
FIG. 18 is a perspective view of the bottom jaw of FIG. 17.

FIG. 17 and FIG. 18 illustrate an embodiment of a jaw 3038 that includes one or more guide members. The jaw 3038 is shown in FIG. 17 as part of an end effector 3040 that includes the jaw 3038 and a second jaw 3042, e.g., an anvil. The one or more guide members can be in the form of opposed substantially vertical sidewalls 3044*a*, 3044*b* configured to engage side of a cartridge received within the jaw 3038, and substantially flat bottom surfaces 3046*a*, 3046*b* on either side of a central longitudinal channel 3048 configured to slidably receive a drive beam, also referred to herein as an "I-beam," through the jaw 3038. A person skilled in the art will appreciate that the vertical sidewalls 3044*a*, 3044*b* may not be precisely vertical, e.g., due to manufacturing tolerances, but nevertheless be considered to be substantially vertical. Similarly, a person skilled in the art will appreciate that the flat bottom surfaces 3046*a*, 3046*b* may not be precisely flat, e.g., due to manufacturing tolerances, but nevertheless be considered to be substantially flat. The substantially flat bottom surfaces 3046*a*, 3046*b* can help provide a better seat for the cartridge within the jaw 3038 for vertically created tissue loads. The substantially vertical sidewalls 3044*a*, 3044*b* can be configured to help minimize cartridge spread, e.g., movement of the cartridge within the jaw 3038 in which it is seated, during fastener deployment, e.g., due to the I-beam slot, which can help provide more robust fastener formation. Cartridge spread can become more pronounced the thicker the tissue being grasped and fastened by the end effector 3040. The substantially vertical sidewalls 3044*a*, 3044*b* can help resist the vertical forces created during movement of the I-beam for fastener deployment and can provide about three times more resistance than sidewalls that are not substantially vertical.

Figure 19:
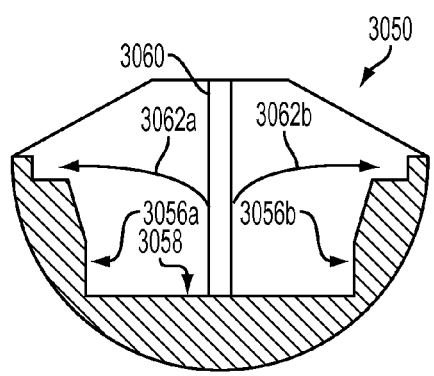
FIG. 19 is a cross-sectional view of another embodiment of a bottom jaw that includes a plurality of guidance features.
Figure 20:
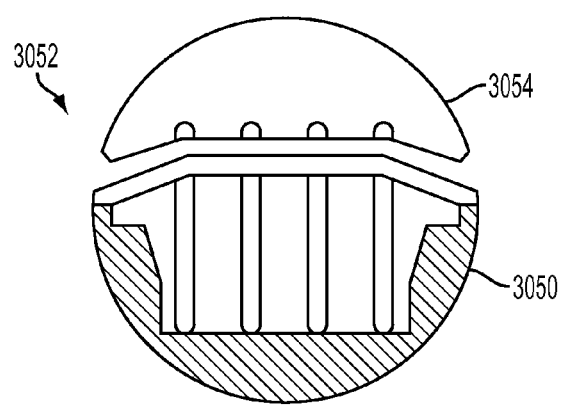
FIG. 20 is another cross-sectional view of the bottom jaw of FIG. 19, the bottom jaw being part of an end effector that also includes an upper jaw.

FIG. 19 and FIG. 20 illustrate another embodiment of a jaw 3050 that includes one or more guide members. The jaw 3050 is shown in FIG. 20 as part of an end effector 3052 that includes the jaw 3052 and a second jaw 3054, e.g., an anvil. The jaw 3050 can be generally configured and used similar to the jaw 3038 of FIG. 17 and FIG. 18. The jaw 3050 in this illustrated embodiment includes one or more guide members in the form of opposed substantially vertical sidewalls 3056*a*, 3056*b* configured to engage side of a cartridge received within the jaw 3050, and a substantially flat bottom surface 3058 along which an drive beam 3060 can be configured to translate through the jaw 3050. FIG. 17 illustrates an embodiment of spreading forces 3062*a*, 3062*b* that the substantially vertical sidewalls 3056*a*, 3056*b* can be configured to counter during fastener deployment.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapling device, comprising:
   an elongate shaft having an end effector coupled to a distal end thereof and including a cartridge-receiving jaw and an anvil pivotally coupled to the cartridge-receiving jaw;
   a staple cartridge disposed within the cartridge-receiving jaw, the staple cartridge having a carrier disposed therein with a plurality of plastically deformable staples formed on the carrier, and the staple cartridge having a deck with a plurality of openings formed therein, each opening being configured to receive one of the plurality of staples therethrough, and each opening having a guide member extending outwardly from the deck and configured to guide a staple being advanced through the opening along an arcuate path.

2. The device of claim 1, wherein each guide member extends outwardly from the deck in a direction toward the anvil.

3. The device of claim 1, wherein each guide member extends outwardly from the deck in a direction away from the anvil.

4. The device of claim 1, wherein each guide member includes opposed sidewalls that engage opposed sides of a staple being advanced therethrough.

5. The device of claim 1, wherein each guide member includes a curved inner surface that guides the staples along a curved pathway.

* * * * *